(12) United States Patent
Ward et al.

(10) Patent No.: US 7,856,324 B2
(45) Date of Patent: *Dec. 21, 2010

(54) AUTOMATIC THRESHOLD SETTING FOR QUANTITATIVE POLYMERASE CHAIN REACTION

(75) Inventors: Lesley Ward, Claremont, CA (US);
Adrian Jensen, New York, NY (US);
Justin Lyon, Indianapolis, IN (US);
Cameron McLeman, Vancouver, WA (US); Bryan Tysinger, Santa Monica, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 718 days.

This patent is subject to a terminal disclaimer.

(21) Appl. No.: 11/646,879

(22) Filed: Dec. 28, 2006

(65) Prior Publication Data

US 2007/0129899 A1 Jun. 7, 2007

Related U.S. Application Data

(63) Continuation of application No. 10/155,877, filed on May 23, 2002, now Pat. No. 7,188,030.

(60) Provisional application No. 60/313,882, filed on Aug. 21, 2001.

(51) Int. Cl.
*G06F 19/00* (2006.01)
*C12P 19/34* (2006.01)

(52) U.S. Cl. ........................................ 702/19; 435/91.2

(58) Field of Classification Search ........................ None
See application file for complete search history.

(56) References Cited

U.S. PATENT DOCUMENTS

| | | | |
|---|---|---|---|
| 6,174,670 B1 | 1/2001 | Wittwer et al. | |
| 6,303,305 B1 | 10/2001 | Wittwer et al. | |
| 6,783,934 B1 | 8/2004 | McMillan et al. | |
| 7,188,030 B2 * | 3/2007 | Ward et al. | 702/19 |
| 2003/0148332 A1 | 8/2003 | Taylor et al. | |

FOREIGN PATENT DOCUMENTS

| | | |
|---|---|---|
| EP | 1 041 158 A2 | 4/2000 |
| EP | 1 138 783 A2 | 4/2001 |

OTHER PUBLICATIONS

Lie et al. Advances in quantitative PCR technology: 5' nuclease assays Current Opinion in Biotechnology vol. 9, pp. 43-48 (1998).*

Held et al., "Real Time Quantitative PCR", Genome Research, Cold Spring Harbor Laboratory Press, Woodbury, NY, vol. 6, No. 10, pp. 986-994, XP 000642795, ISSN: 1088-9051 (Oct. 1996).

Higuchi et al., "Kinetic PCR Analysis: Real-time Monitoring of DNA Amplification Reactions", BioTechnology, Nature Publishing Co., NY, vol. 11, No. 9, pp. 1026-1030, XP-000197685, ISSN: 0733-222X (Sep. 1993).

Woudenberg et al, *Quantitative PCR by Real Time Detection*, SPIE vol. 2680, pp. 306-315 (1996).

Lie et al., *Advances in Quantitative PCR Technology: 5' Nuclease Assays, Analytical Biotechnology*, pp. 43-48 (1998).

Peccoud et al., *Statistical Estimations of PCR Amplification Rates*, pp. 1-17.

Rasmussen et al., *Quantitative PCR by Continuous Fluorescence Monitoring of a Double Strand DNA Specific Binding Dye*, Biochemica, No. 2, pp. 8-11 (1998).

Nitsche et al., *Different Real-Time PCR Formats Compared for the Quantitative Detection of Human Cytomegalovirus DNA*, Clinical Chemistry, 45:11, (1932-1937, 1999).

Grove, *Quantitative Real-Time Polymerase Chain Reaction for the Core Facility Using TaqMan and the Perkin-Elmer/Applied Biosystems Division 7700 Sequence Detector*, ABRF, pp. 1-11, (1999).

Roche Molecular Biochemicals Technical Note No. LC 11/2000, *Absolute Quantification with External Standards*, Roche, pp. 1-20.

Giulietti et al., *An Overview of Real-Time Quantitative PCR: Applications to Quantify Cytokine Gene Expression*, Methods, vol. 26, pp. 386-401, Elsevier Science (USA) (2001).

Applied Biosystems, *User Bulletin #2, ABI Prism 7700 Sequence Detection System*, pp. 1-36, (Dec. 11, 1997).

Yajima et al., *Quantitative Reverse Transcription-PCR Assay of the RNA Component of Human Telomerase Using the TaqMan Fluorogenic Detection System*, Clinical Chemistry 44:12, pp. 2441-2445, (1998).

Winer et al., *Development and Validation of Real-Time Quantitative Reverse Transcriptase-Polymerase Chain Reaction for Monitoring Gene Expression in Cardiac Myocytes in Vitro*, Analytical Biochemistry, vol. 270, No. 1, pp. 41-49(9) (May 1999), abstract only.

(Continued)

*Primary Examiner*—John S Brusca

(57) ABSTRACT

Disclosed are systems and methods for identifying and quantitating the presence of one or more DNA species in a sample population through PCR amplification. DNA species quantitation includes a determination of a threshold fluorescence value used in the assessment of the PCR amplification reaction. Various embodiments of the present invention incorporate an enhancement function useful in selecting appropriate threshold fluorescence values and facilitate the determination of DNA concentrations by quantitative PCR based methodologies.

38 Claims, 9 Drawing Sheets

OTHER PUBLICATIONS

Freeman et al., *Quantitative RT-PCR: Pitfalls and Potential*, BioTechniques, vol. 26, No. 1, pp. 112-125, (1999).

Bustin, *Absolute Quantification of mRNA Using Real-Time Reverse Transcription Polymerase Chain Reaction Assays*, Journal of Molecular Endocrinology, vol. 25, pp. 169-193, (2000).

Saraswathy et al., *Human Immunodeficiency Virus Type 1 Subtypes Among Malaysian Intravenous Drug Users*, Southeast Asian J. Trop Med. Public Health, (Abstract), vol. 31, No. 2, pp. 283-286, (2000), Abstract only.

Rostaing et al., *Changes in Hepatitis C Virus RNA Viremia Concentrations in Long-Term Renal Transplant Patients after Introduction of Mycophenolate Mofetil*, Transplantation, vol. 15, No. 69(5), pp. 991-994 (Abstract), (Mar. 15, 2000), Abstract only.

Roche Applied Science Technical Note No. LC 13/2001, *Relative Quantification*, pp. 1-28.

Morin et al., *Laboratory for Conservation Genetics, Leipzig*, Molecular Ecology, vol. 10, pp. 1835-1844, as reproduced at www.rateDNA.com, (2001).

Alexandersen et al., *The Early Pathogenesis of Foot-and-Mouth Disease in Pigs Infected by Contact A Quantitative Time-Course Study Using TaqMan RT-PCR*, Gen Virol, vol. 82, (pt 4), pp. 747-755, (Abstract), (2001), Abstract only.

Levis et al., *Strategy for the Maximization of Clinically Relevant Information from Hepatitis C Virus*, RT-PCT Quantification, J. Clin. Virol, vol 20, No. 3, pp. 163-171, (2001), Abstract only.

Pfaffl, *A New Mathematical Model for Relative Quantification in Real-Time RT-PCR*, Nucleic Acids Research, vol. 29, No. 9, p. e45, (2001), Abstract only.

Livak, et al., *Analysis of Relative Gene Expression Data Using Real-Time Quantitative PCR and the $2^{-\Delta\Delta C_T}$ Method*, Methods, vol. 25, pp. 402-408, (2001).

Bustin, *Quantification of mRNA Using Real-Time Reverse Transcription PCR (RT-PCR): Trends and Problems*, Journal of Molecular Endocrinology, vol. 29, pp. 23-39, (2002).

Ginzinger, *Gene Quantification Using Real-Time Quantitative PCR: An Emerging Technology Hits the Mainstream*, Elsevier Science Inc., Experimental Hematology, vol. 30, pp. 503-512, (2002).

Morrison et al., *Nanoliter High Throughput Quantitative PCR*, Nucleic Acids Research, vol. 34, No. 18, pp. 1-9 and e 123, (2006).

Applied Biosystems, *Data Analysis on the ABI PRISM® 7700 Sequence Detection System: Setting Baseline and Thresholds*, pp. 1-12, (2002).

"LightCycler Relative Quanitification Software", Roche Molecular Biochemicals, Version 1.0, Mar. 2001.

"LightCycler Absolute Quanitification with External Standards", Roche Molecular Biochemicals, Technical Note No. LC 11/2000.

\* cited by examiner

AUTOMATIC THRESHOLD SETTING FOR QUANTITATIVE POLYMERASE CHAIN REACTION

CROSS-REFERENCE TO RELATED APPLICATIONS

This application is a continuation of U.S. patent application Ser. No. 10/155,877 filed May 23, 2002, which claims the benefit of prior Provisional Application No. 60/313,882, filed Aug. 21, 2001, both of which are incorporated herein in their entireties by reference.

BACKGROUND

1. Field

Aspects of the present invention generally relate to nucleic acid analysis, and more particularly, to a system and method for determining the quantity of a particular target within a PCR reaction.

2. Description of Related Art

Polymerase Chain Reaction (PCR) is a methodology routinely used in the amplification of genetic material from template nucleotide strands or fragments. Recently, a PCR-based method known as quantitative PCR has been developed to identify target nucleotide strands or fragments in a sample population. To determine the concentration of a specific target initially present, this method utilizes a labeling dye which fluoresces in proportion to the amount of target DNA species that is produced by the PCR reaction. Two principal determinants in the accurate and reproducible quantitation of the initial target concentration are a noise assessment and a threshold value determination. The noise assessment reflects the changing reaction conditions and environment during the PCR reaction and is used to determine when target amplification is sufficiently above a background signal to enable accurate measurement of the fluorescence of the amplified target. The threshold value reflects the change in fluorescence during the PCR reaction and is typically identified as a statistically significant region above a noise baseline. Identification of the threshold value is important as it reflects the portion of the PCR reaction where a sufficient level of amplification has been achieved to allow for calculation of the initial target concentration. Conventional methods used to identify the threshold value may be subject to undesirable variability which in turn affects the accuracy of the quantitation results. Furthermore, a number of conventional threshold selection techniques rely on manual interpretation or user-based identification techniques. As a result, these methods may suffer from diminished accuracy and reproducibility. Currently, there is a need for an automated threshold selection function which overcomes the limitations associated with conventional threshold value selection techniques. Improvement in the method by which this value is identified may reduce the degree of uncertainty or variability in determining the concentration of target in the sample and improve the analytical performance of quantitative PCR.

SUMMARY OF THE INVENTION

The present invention satisfies aforementioned needs for an improved threshold value selection function that may be used in conjunction with analytical methodologies such as quantitative PCR, real-time PCR, quantitative competitive PCR and other amplification methodologies requiring determination of an exponential reaction region. The method by which the threshold value is selected may be readily integrated into a computer program and/or control system used in conjunction with instrumentation used to perform quantitative PCR allowing for more complete automation.

In one aspect, the threshold value selection function comprises a novel method for identifying an exponential region of an amplification plot used in a quantitative PCR reaction. The exponential region is identified, in part, by enhancing and extending linear regions of the amplification plot using a highest-slope assessment approach. The exponential region for a plurality of reactions may be averaged using a convolved Gaussian analysis to obtain a combined threshold value. Gaussian analysis in this manner further provides a means for assessing the accuracy or appropriateness of the identified threshold.

Alternatively, the combined threshold for the plurality of amplification reactions may be obtained by taking the average of the thresholds for the individual reactions. Subsequently, a quality assessment metric is used to determine if the selected threshold values produce acceptable quantitation results.

Various embodiments of the disclosed fluorescence analysis methods are suitable for implementation using computers, hardware devices or instrumentation which may be desirably configured to provide for automated analysis and, in certain implementations, may be used to more accurately quantify the initial concentration of the target than conventional methodologies. In one aspect, various embodiments of the disclosed system and methods can provide one or more advantages over existing methods for PCR quantification as they are not dependent on experimenter selection or interpretation which may introduce undesirable errors or bias into the results. Instead, various embodiments of the invention provide for more complete automation of quantitative PCR to provide rapid and substantially accurate determination of experimental results.

In one aspect, the invention comprises a method for identifying a threshold value to be used in the analysis of an amplification reaction, the method comprising the steps of: Performing a PCR-based amplification using a target sequence having an initial concentration and containing a detectable reporter construct; Acquiring detection information generated by the detectable reporter construct indicative of a change in the concentration of the target sequence over the course of the PCR-based amplification; Assembling a data set comprising at least a portion of the detection information to model amplification reaction characteristics; and Performing an exponential region analysis on the data set using a sliding window procedure to identify an exponential threshold which reflects the modeled amplification reaction characteristics in a region where the target sequence concentration is increasing in a substantially exponential manner.

In another aspect, the invention comprises a method for generating a combined threshold for a quantitative PCR-based analysis wherein a plurality of sample templates are amplified using a fluorescent reporter construct to monitor the progress of amplification, the method comprising the steps of: Acquiring fluorescence data corresponding to the amplification for each of the plurality of sample templates; Analyzing the fluorescence data to generate a plurality of amplification profiles; Applying a Gaussian approximation to each of the amplification profiles to identify an exponential region of amplification corresponding to a threshold value for each sample template; and Performing a Gaussian convolution using the threshold values to generate the combined threshold.

In still another aspect, the invention comprises a method for determining a noise region for a PCR reaction whose amplification profile is modeled by a plurality of data points, the method further comprising the steps of: Identifying an initial noise region corresponding to a subset of the data points; Generating a baseline value for the initial noise region by performing a linear regression analysis on the subset of data points; Subtracting the baseline value from the amplification profile to generate an adjusted data set; Performing a serial monotonicity analysis using the adjusted data set to identify the boundary of the noise region; and Identifying a transition data point along the boundary of the noise region to define the starting position for an exponential region of the amplification profile.

In another embodiment, the invention comprises a method for approximating the exponential region for an amplification plot comprising a plurality of data points defining a data set, the method comprising the steps of: Performing a regression fit on the data set by sequentially defining a plurality of line segments that are each fit between a defined number of the data points; Identifying a best-fit line from the plurality of line segments that possesses a slope which exceeds the other line segments fit between the defined number of data points while maintaining a quality of fit threshold; Defining a second number of data points for which a plurality of line segments are fit according to steps of regression fitting and best-fit line identification to generate a second best-fit line; Determining which best-fit line has the greatest slope; Repeating the steps above for one or more additional defined numbers of data points until a best line with the greatest slope is determined; and Associating the best line determined with the exponential threshold.

In a still further embodiment, the invention comprises a system for determining threshold values for quantitative PCR, the system comprising: A reaction module used to perform PCR amplification of at least one sample template using a detectable reporter label; A data collection module that detects reporter label intensities over the course of the PCR amplification of the at least one sample template; and A data processing module that: receives the detected intensities for each sample template and generates an amplification profile to model the PCR amplification for the sample template; identifies a noise baseline for each amplification profile; identifies an exponential threshold value for each amplification reaction; and identifies a combined threshold value representative of the associated threshold values for each amplification reaction.

In yet another embodiment, the invention comprises a system for identifying a fluorescence threshold for at least one sample template, the system comprising: A reaction module where PCR amplification of the at least one sample template takes place using a detectable reporter label; A data collection module that detects reporter label intensities over the course of the PCR amplification and reports the detected intensities; and A data processing module that receives the detected intensities, associates the detected intensities with a data set, performs a noise region analysis on the data set, and thereafter performs an exponential region analysis on the data set to generate a threshold value for each of the sample templates.

In another aspect, the invention comprises a method for generating a combined threshold for a quantitative PCR-based analysis wherein a plurality of sample templates are amplified using a fluorescent reporter construct to monitor the progress of amplification, the method comprising the steps of: Acquiring fluorescence data corresponding to the amplification for each of the plurality of sample templates; Analyzing the fluorescence data to generate a plurality of amplification profiles; Applying a threshold approximation to each of the amplification profiles to identify an exponential region of amplification corresponding to a threshold value for each sample template; and Averaging the threshold values to generate the combined threshold.

BRIEF DESCRIPTION OF THE DRAWINGS

The computer program listing appendix is available on Public Pair in the supplemental content section of this application or patent.

These and other aspects, advantages, and novel features of the invention will become apparent upon reading the following detailed description and upon reference to the accompanying drawings. In the drawings, similar elements have similar reference numerals.

Figure 1:
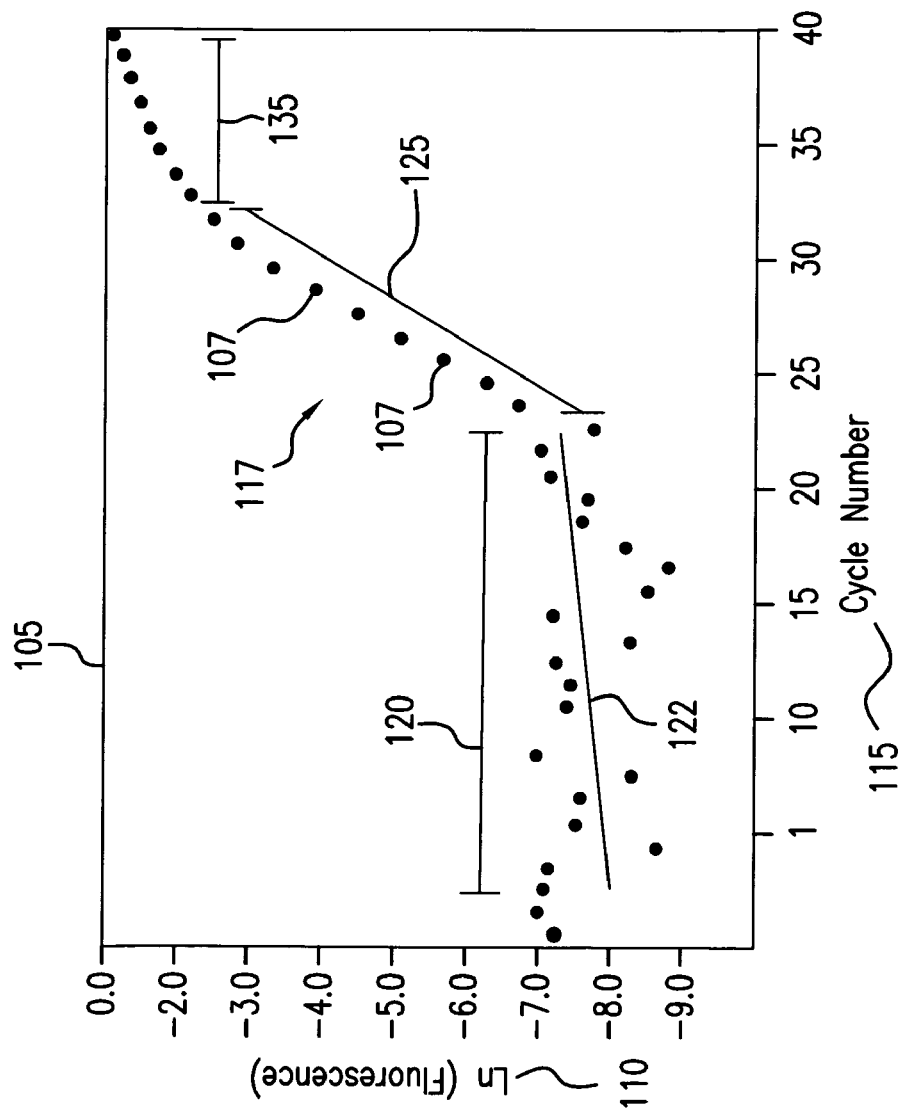
FIG. 1 is a graph illustrating an exemplary amplification plot for a quantitative PCR reaction.

The computer program listing appendix is a source code listing for an exemplary threshold selection program.

DETAILED DESCRIPTION OF CERTAIN EMBODIMENTS

Reference will now be made to the drawings wherein like numerals refer to like elements throughout.

In general, amplification of a target template DNA strand by polymerase chain reaction (PCR) proceeds through a series of temperature regulated cycles using the activity of a thermostable enzyme and a sequence specific primer set. At an appropriate temperature, the primers hybridize to portions of the target DNA strand and the enzyme successively adds a plurality of nucleotide bases to elongate the primer which results in the production of progeny (daughter) strands. Each progeny strand possesses a complementary composition relative to the target template strand from which it was derived, and can serve as a template in subsequent reaction cycles.

When applying quantitative methods to PCR-based technologies a fluorescent probe or other detectable reporter construct is incorporated into the reaction to provide a means for determining the progress of the template amplification. In the case of a fluorescent probe, the reaction fluoresces in relative proportion to the quantity of DNA product produced. The TaqMan™ procedure (Applied Biosystems, CA) describes one such fluorescent methodology for performing Quantitative PCR. Briefly described, this system integrates the use of a detectable reporter construct, or probe, which comprises both a fluorescent label molecule and a quencher molecule. Ordinarily, the quencher nullifies the majority of fluorescence which may be emitted by the probe. During the amplification process, however, the quencher molecule is released from the probe allowing the fluorescent label to be detected. The quantity or intensity of fluorescence may then be correlated with the amount of product formed in the reaction. Using this information, calculations can be made to determine the initial quantity of template present. Quantitation in this manner is useful in applications including: determination of levels/concentrations of specific DNA and RNA sequences in tissue samples, identification of viral loads, genotyping, and numerous other applications. For additional information regarding the fundamental concepts of quantitative PCR the reader is directed to *Allelic Discrimination by Nick-Translation PCR with Fluorogenic Probes*, L. G. Lee, C. R. Connell, and W. Bloch, Nucleic Acids Research 21:3761-3766, 1993 and *PCR Technology: Principles and Applications for DNA Amplification*. Karl Drlica, John Wiley and Sons, 1997.

Over the course of amplification of the target, the reaction kinetics typically change such that the amount of product formed does not necessarily increase at a constant rate. For example, during the early stages of a PCR reaction there is an approximate doubling of the nucleotide strands with each cycle. In the later stages of the reaction, however, the efficiency of the amplification process is markedly reduced resulting in non-exponential amplification. Without committing to any particular theory, factors that may affect amplification efficiency can include limiting quantities of reagents and competition for reaction products. As a result, it is often necessary to monitor the reaction at various intervals and acquire data which relates to the fluorescence of the reaction at these intervals. Using this information graphs, plots, or other data analysis methods may be used to analyze the fluorescence intensity measurements and determine the initial concentration of template present during the onset of the reaction.

FIG. 1 illustrates an exemplary amplification plot 105 depicting the reaction characteristics for a typical DNA template. The amplification plot 105 comprises a plurality of fluorescence data points 107 forming an amplification profile 117. In the amplification plot 105, the y-axis values 110 correspond to observed fluorescence (logarithmic scale). The x-axis values 115 correspond to the cycle number of the PCR reaction for which the reaction fluorescence is observed. This information relates the intensities of observed fluorescence in an amplification reaction to the cycle number and is used to track the production of progeny strands from the initial sample template.

When analyzing the amplification profile 117 various regions are desirably identified which are subsequently used in calculations for determining the initial concentration of template present in the reaction. A common problem with conventional methods is that they require an operator or experimenter to visually evaluate and interpret the fluorescence data in order to identify the relevant regions of the amplification profile 117. This manner of manual selection is undesirable as it is subjective, error prone, and may degrade the quality of subsequent quantitative analysis. The present invention overcomes these problems and drawbacks through the use of methods designed to identify the regions of the amplification profile in an objective and reproducible manner.

During the earlier cycles of the reaction, the observed fluorescence may be erratic and not necessarily correspond to an exponential increase. This region generally corresponds to a noise region 120 where the amount of fluorescence produced by the amplification reaction cannot be readily distinguished from background and/or non-specific fluorescence produced by the instrumentation and detection equipment.

Reaction fluorescence data in the noise region 120 is desirably identified to avoid quantitation calculations which use these values directly as they may lead to inaccurate results. When analyzing the amplification plot 105 it is useful to identify the range and limits of the noise region 120 so that this area may be distinguished from other regions of the amplification profile 117 which may more accurately reflect the true fluorescence of the desired products of the reaction. Furthermore, identification of the noise region 120 can be used to "normalize" the data contained in the amplification profile 117. Identification of the noise region 120 of the amplification profile 117 further comprises determining a baseline 122 which is fit to the data extending through the noise region 120. The baseline 122 typically has a small positive slope and may be subtracted from raw fluorescence data to convert the data into corrected measurements of fluorescence intensity. In performing this operation, instrument-generated errors as well as background fluorescence can be effectively reduced thereby improving the accuracy and sensitivity of the quantitation of initial template concentration.

An exponential region 125 of substantially increasing fluorescence follows the noise region 120. Within the exponential region 125, the detected quantity of fluorescence is sufficient to overcome that generated in the noise region 120. The characteristics of the amplification reaction during the cycles associated with the exponential region 125 reflect desirable reaction kinetics that can be used to perform quantitative template calculations. As will be described in greater detail herein below, a significant advantage of the present invention is the ability to identify the exponential region 125 in an automated manner and select at least a portion of it to be used in determining the initial template concentration.

As shown in FIG. 1, the exponential region 125 may be followed by a plateau region 135 where the reaction is no longer increasing in an exponential manner. Typically, the plateau region 135 occurs in the later cycles of the reaction and results from depletion of primers or reagents. When performing quantitation calculations, it is useful to distinguish the exponential region 125 from the plateau region 135 to avoid erroneous or non-representative quantitation values. As with distinguishing the noise region 120 from the exponential region 125, the methods described herein similarly distinguish the plateau region 135 from the exponential region 125 to improve the quality of the resultant calculations that make use of this information.

Figure 2:
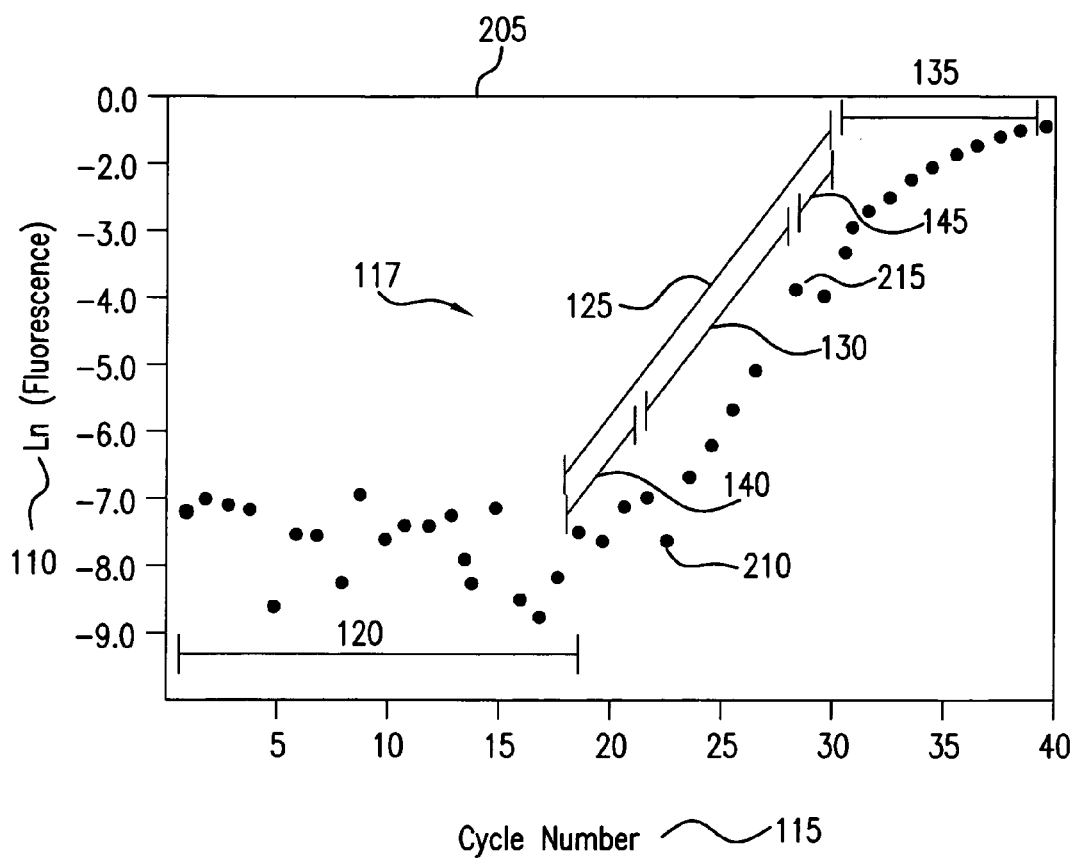
FIG. 2 is a graph illustrating another exemplary amplification plot containing aberrant data points.

In some instances when generating an amplification profile there may be one or more data points which do not conform to the trend established by surrounding data points. These aberrant data points form "kinks" in the amplification plot and may present problems in identifying the various regions within the amplification profile. FIG. 2 illustrates an exemplary amplification plot 205 having a kinked structure. Two aberrant data points 210, 215 are observed within the amplification profile 117 and are located in the exponential region 125. The first aberrant data point 210 is located slightly outside of the noise region 120 within the early portion of the exponential region 125.

In one aspect, the beginning of the exponential region 125 may be determined by identifying a trend of increasing fluorescence which occurs over a specified range of the amplification profile 117. This approach, often termed as a monotonicity test, may be undesirably biased by the presence of the kinks 210, 215. As a result, the limits and range of the exponential region 125 may be improperly identified when one or more kinks 210, 215 are present in the amplification profile. For example, as shown in the amplification plot 205, a truncated exponential region 130 is formed by the region of the amplification profile between the kinks 210, 215. Useful data 140, 145 corresponding to additional portions of the exponential region outside of the truncated region 130 may further be undesirably discarded or inappropriately associated with either the noise region 120 or the plateau region 135. Various embodiments of the present invention overcome this limitation and are able to distinguish aberrant data points 210, 215 to thereby substantially identify the exponential region 125. The identified exponential region 125 may then be desirably used in subsequent calculations to estimate the initial concentration of sample template within the reaction.

Unlike conventional methods which subjectively assess the amplification profile 117 to identify the various regions 120, 125, 135, the present invention provides a means for rapidly and reproducibly identifying each region, in many instances with greater accuracy than can be obtained by visual inspection of the amplification profile 117. Furthermore embodiments of this method are tolerant of "imperfect" data sets and can overcome potential errors in selecting the bounds of each region 120, 125, 135 when one or more of the fluorescence data points 107 are skewed above or below an expected value.

Another advantage of the invention is that these methods may be readily integrated into software applications and computer hardware that may perform the baseline determination in an automated manner without user intervention. This feature of various embodiments of the invention can improve the performance and accuracy of quantitative PCR-based methods and can allow for more complete automation of the identification of initial template concentrations.

Figure 3:
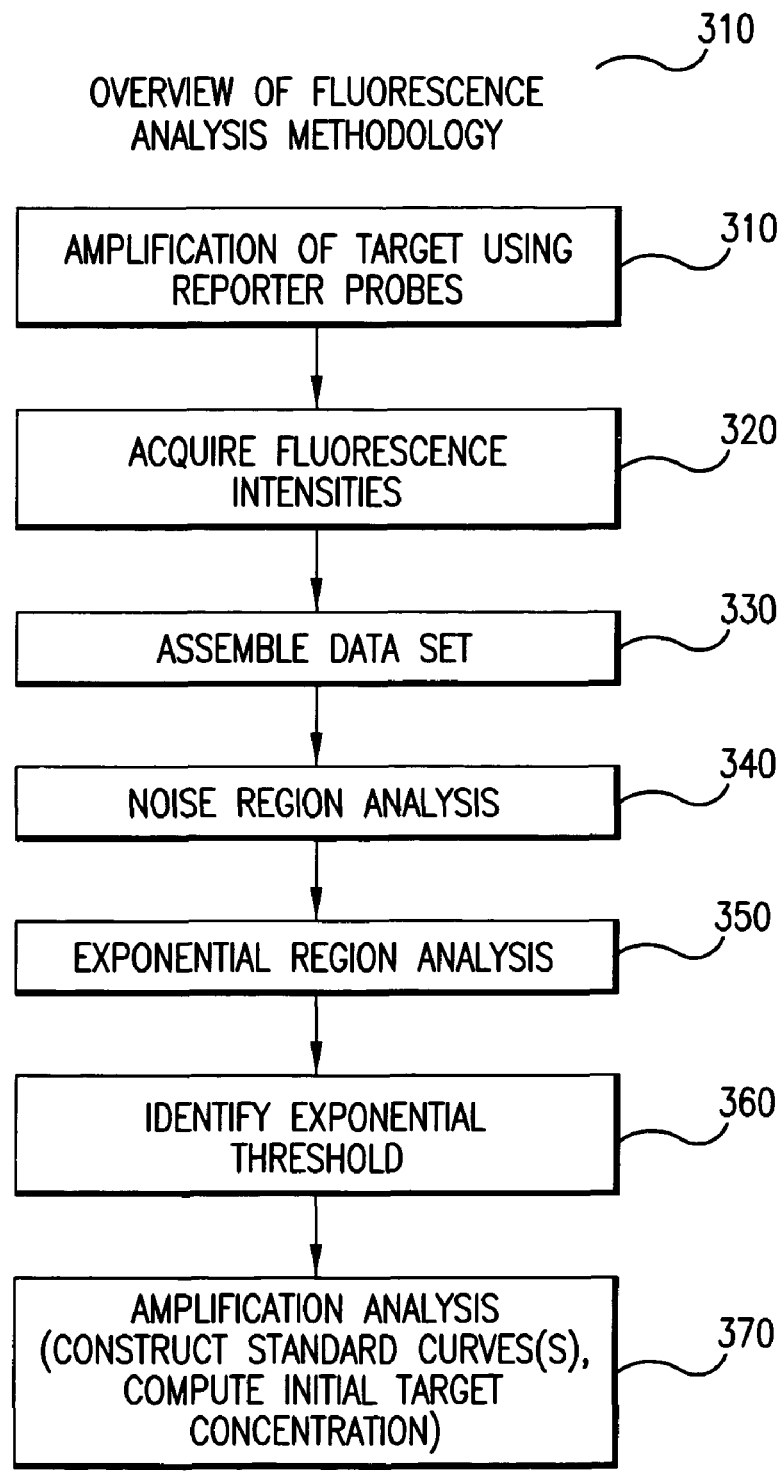
FIG. 3 is a flowchart illustrating an overview of a fluorescence analysis method.

FIG. 3 illustrates a fluorescence analysis process 300 which, according to various embodiments, can be used in conjunction with quantitative PCR-based methods. As previously discussed, the process 300 commences with the amplification of a target strand or fragment 310. A fluorescent reporter molecule is used to track the progress of the amplification reaction by generating a fluorescence signal in relative proportion to the amount of synthesized product. Fluorescence intensities are acquired 320 over the course of the amplification reaction and are typically sampled at constant intervals that may correspond to incremental cycles of the amplification reaction. For each amplification reaction, a data set is assembled 330 which reflects the collection of observed fluorescence intensities. The data set is typically stored in a file where it may be organized in numerous different ways. In various embodiments, the data set comprises a collection of numerical intensity values that are organized in a table or spreadsheet for ease of visualization and manipulation. Additionally, graphical methods can be applied to the data set to generate amplification plots and charts.

Following data collection and storage, the fluorescence data is input into a process where the noise region of the amplification reaction is identified 340. As previously described it is during this stage that the bounds of the noise region are defined thus identifying fluorescence data points that may not be suitable for direct quantitation calculations. Furthermore, during noise region identification 340, the noise baseline 122 is established and may be used in subsequent data analysis, for example, to normalize the data and identify the boundary where quantitation calculations can be made. Additional details of the noise region identification 340, according to various embodiments, will be described in greater detail with reference to FIG. 4.

Following identification of the noise region 340, the process 300 proceeds to evaluate the exponential region 350 of the amplification reaction. Due to the importance of selecting the exponential region, specialized methods are utilized to increase the degree of confidence that the bounds of the exponential region are appropriately identified. Furthermore, as will be described in greater detail below with reference to FIGS. 5 and 6, analysis of the exponential region entails rigorous evaluation of the characteristics of the amplification profile 117 to identify one or more sub-regions which are used in selecting an exponential threshold 350. In one aspect, the exponential threshold 350 is selected to reside at the approximate midpoint of the intensity values that may occur over a selected range of cycles. Furthermore, the threshold 350 may be representative of the region of the amplification profile that corresponds to a substantially exponential increase in the concentration of the template. Selection of an appropriate exponential threshold 350 is an important consideration to maintain the accuracy of subsequent analytical calculations. Various embodiments of the present invention provide a novel process for exponential threshold identification which takes into account numerous factors which affect the ultimate quality of the quantitative analysis and provide a method for selecting this value in an objective and reproducible manner.

After the exponential threshold has been selected 360, the fluorescence analysis process may store this value and proceed to other analytical steps 370. Conventional quantitative analysis procedures may be readily adapted to receive the identified exponential threshold value and use this information to compute the initial target concentration.

Figure 4:
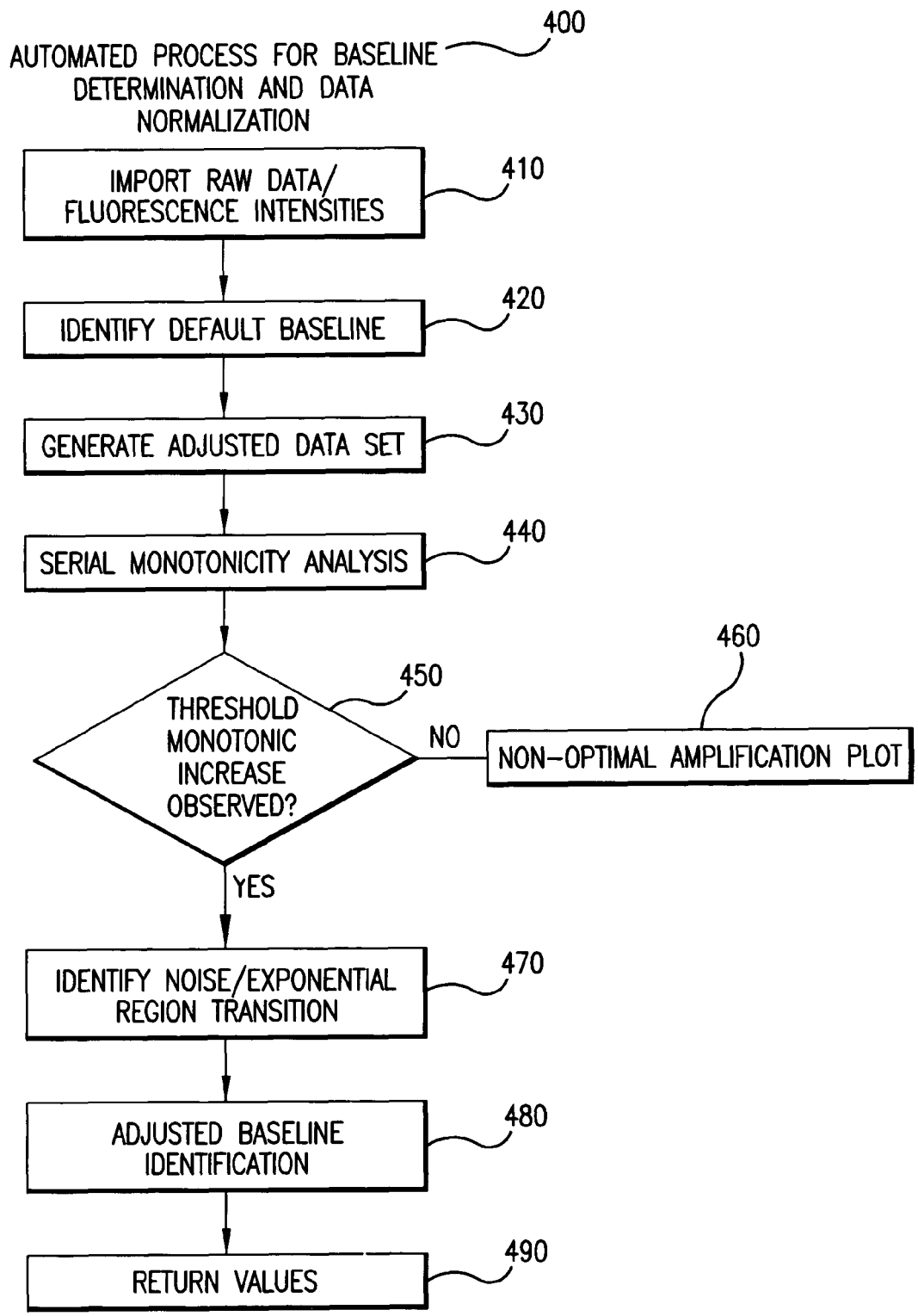
FIG. 4 is a flowchart illustrating one embodiment of a method for automated baseline determination.

FIG. 4 illustrates a method, according to various embodiments, for baseline analysis 400 used to identify the noise region 120 and baseline 122 of the amplification plot 105, 205. In one aspect, this method overcomes one or more potential problems associated with the presence of aberrant data points 210, 215 in the amplification profile 117 by identifying a threshold region of monotonic increase. Should such a region be present in the amplification profile 117, an end point to the noise region 120 can be assigned and the exponential region 125 differentiated despite the potential presence of the one or more aberrant data points 210, 215.

According to various embodiments, the baseline analysis 400 commences by receiving fluorescence data 410 previously acquired from an amplification reaction. Using the fluorescence data, the baseline 122 may be identified 420 by selecting an initial boundary set which may be defined by a first and last cycle number. An interpolated line representing the baseline 122 is then fit between the data points of the initial boundary set using conventional "best-fit" analysis methods.

In one aspect, the first and last cycle numbers defining the bounds of the initial boundary set are pre-selected. Based on the characteristics of a typical amplification reaction, the first cycle number may be selected to reside between approximately cycle number "0" and cycle number "10". Likewise, the second cycle number may be selected to reside between approximately cycle number "10" and cycle number "20". By way of example, the initial boundary set may comprise a first cycle defined by cycle "3" of the amplification reaction and a second cycle defined by cycle "15" of the amplification reaction. It will be appreciated that the selection of the first and last cycle numbers used to define the initial boundary set is not limited to the aforementioned values and other values may be readily selected to generate suitable initial boundary set limits.

In one aspect, the initial boundary set comprises data points between the selected cycles through which the baseline 122 is fit to represent an approximation of the noise level in the initial boundary set. In a subsequent analytical stage 430, the baseline 122 is then subtracted from the fluorescence data of the amplification plot to generate an adjusted data set. The adjusted data set at least partially compensates for the calculated noise region 120 and a monotonicity test may be applied to the data to determine the commencement of the exponential region 125 of the amplification profile 117. The monotonicity test identifies a sequence of increasing fluorescence values which marks the transition of the amplification profile from the noise region 120 to the exponential region 125. Using this test, the first cycle after which the adjusted amplification profile is determined to be monotonically increasing is identified as the start of the exponential region 125.

While a simple monotonicity test desirably eliminates fluctuations or variations found in the noise region 120, a potential problem arises when the amplification profile 117 contains one or more aberrant data points. In a case such as this, the simple monotonicity test may undesirably discard data near an aberrant data point (i.e. eliminate information behind a kink in the amplification profile). Thus, if a kink is formed by aberrant data present in the plateau region 135, there is the potential for the loss of much of the relevant information about the curve including a large portion of the exponential region 130.

Various embodiments of the present invention can overcome this problem by applying a serial monotonicity analysis 440 to the adjusted data set. The serial monotonicity analysis 440 identifies strings of monotonically increasing data points (a monotonic run) present within the adjusted data set. The length of each string (defined by the number of cycles contained in the string) is compared to a preselected monotonic run number 450 which corresponds to a minimum number of cycles of continuous increase in fluorescence over a period of time. The first string, which is at least as long as the monotonic run number, identifies the transition point marking the end of the noise region 120 and the beginning of the exponential region 125. In one aspect, the value of the monotonic run number corresponds to approximately seven consecutive cycles of monotonic increase however this value may be altered as needed to accommodate different desired analytical constraints.

An amplification profile 117 which does not possess a monotonic string at least as large as the selected run number may be considered to contain only a noise region 120 and lack the required exponential region 125 needed to perform accurate quantitation calculations. Those amplification plots which do not meet the monotonic run number criteria are flagged as non-optimal 460 and may be removed from further analysis by the method 400. If the amplification profile 117 contains a string at least as long as the monotonic run number, the first cycle or data point in the string corresponding to the monotonic increase is designated as the transition point 470 between the noise region 120 and the exponential region 125. Through the use of this method 400, the bounds of the noise region 120 may be more accurately identified since it is a highly unlikely occurrence for the adjusted noise region to contain a period of monotonic increase that is at least as large as the selected run number. Subsequently, a second adjusted baseline may be established 480 by evaluating the noise region identified by the serial monotonicity test using a best fit methodology as before. Alternatively, the original default baseline may be assessed to determine if it is suitable for use in quantitative calculations or if the data set contains non-uniform or kinked data.

As previously noted, one feature of various embodiments of the baseline analysis methodology 400 is that it provides a means for overcoming certain problems associated with analysis of amplification profiles containing kinked data points. Once a monotonic increase of the proper size and duration has been identified, subsequent decreases in fluorescence after the increase may be viewed as kinks rather than a continuation of the noise region 120. This feature allows for more accurate baseline determination and can be adapted to automated methods without the need for experimenter interpretation. Following the determination of both the baseline 122 and the transition between the noise 120 and exponential regions 125, the method 400 may return these values 490 to be used in subsequent calculations including detailed exponential region assessment.

In order to perform the calculations associated with quantitative PCR, large amounts of fluorescence data are generally collected and analyzed. In one aspect, the fluorescence data comprises information from one or more amplification reactions that is desirably associated. For example, in a typical analysis, a plurality of replicate amplification reactions are performed (duplicate, triplicate, etc). Additionally, one or more known concentration templates (standards) may be amplified along with samples of unknown concentration. The standard templates and replicate assays may be used in the identification of the sample concentration and to aid in establishing the accuracy of the calculated values. Various embodiments of the present invention readily accommodate the evaluation of large quantities of information and may be configured to operate with complex data sets containing information from many amplification reactions that may be simultaneously analyzed.

When evaluating the fluorescence data generated by an amplification reaction, a collection of intensity values may be obtained for the reaction that generally correspond to the observed fluorescence at various times during the reaction and may be further related to particular amplification cycles. The fluorescence data is desirably collected and analyzed over at least a portion of the amplification reaction which, for example, may correspond to the time between the first cycle and the last cycle of the reaction. While this data can be plotted and interpreted manually, it is desirable to simplify the data by representing it in a compact equation form. According to various embodiments, each amplification reaction is analyzed by attributing a series of line segments with the curve (amplification profile) formed by a particular data set. This approach to data analysis allows for the selection of a suitable exponential region to be used in determining the initial concentration of sample template.

Figure 5:
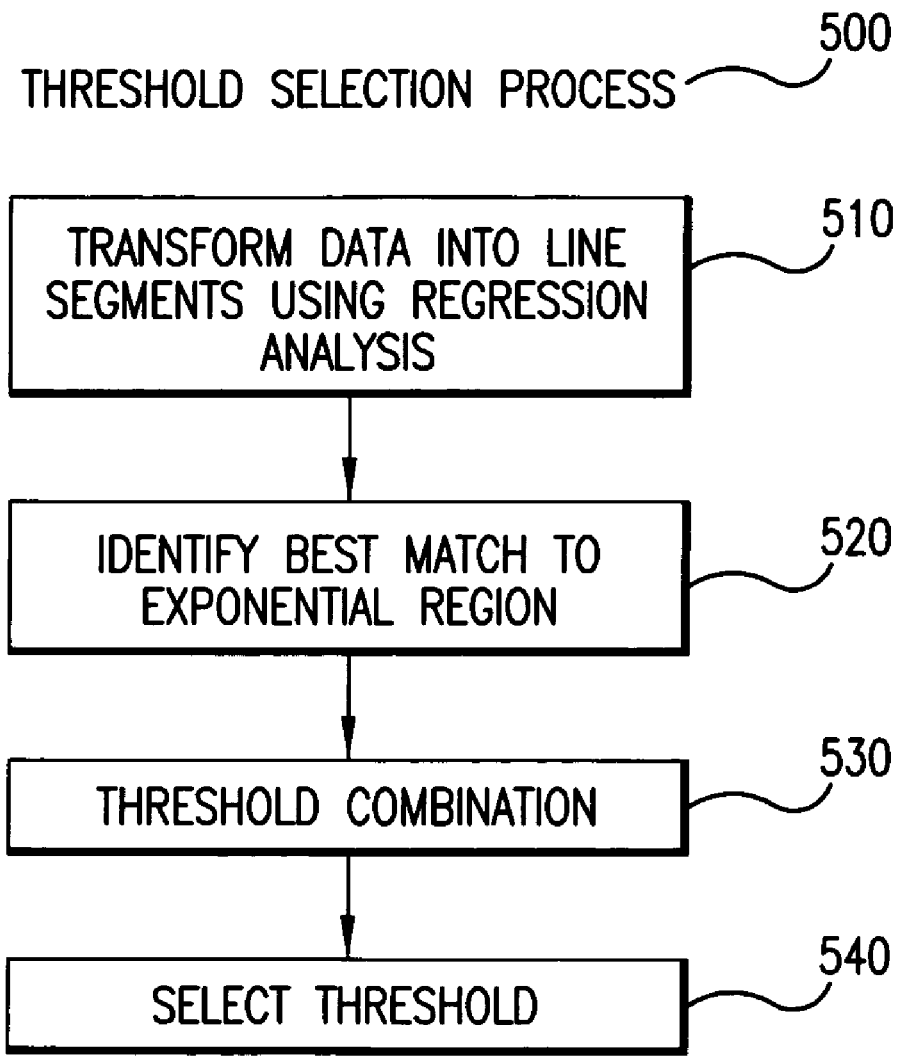
FIG. 5 is a flowchart illustrating one embodiment of a threshold selection process.

FIG. 5 illustrates an overview, according to various embodiments, of a threshold selection process 500 for determining the exponential region for an amplification profile 117 which provides enhanced analysis of the fluorescence data. This method 500 is applied to one or more associated fluorescence data sets and is used to individually assess each data set and combine the results to permit complete quantitative analysis of the sample template(s). The process 500 commences with a modified linear least-squares regression fit 510 of the fluorescence data for each amplification reaction. In one aspect, the regression fit 510 is applied to the data represented in a log-linear plot using variable-length windows of consecutive data points along the amplification profile 117. Briefly described, upon identifying the bounds of the noise region 120, for example, by the serial monotonicity test 400, the regression fit 510 is performed by fitting a plurality of lines to regions of the data outside of the noise region 120 (defining, in part, the exponential region). Each line is designated to have a length from between, for example, approximately 3 through 7 cycles. The exponential region 125 of the amplification profile 117 is identified by finding a line with a high slope and high accuracy of fit. This line is then extended to maximize the slope while maintaining a desired minimum fit accuracy.

One desirable feature of the regression fit 510 is that identification of the best fit line segment to the log-linear plot additionally provides a means to select the region of enhanced exponentiality 520 which may be subsequently used in calculations relating to the quantitative identification of the initial sample template concentration. When selecting the best match to the exponential region 520, desirable characteristics of the line segment to be associated with the exponential region include: (a) a high fit quality, (b) a steep slope, and (c) a long cycle length. As will be described in greater detail herein below, a line segment that possesses these characteristics may be used to model the exponential region 125 of the amplification profile 117. A more complete discussion of the regression fit methodology and approximation of the exponential region 125 is described in detail in connection with FIGS. 6 and 7.

Upon selecting the line segment to be associated with the exponential region 125 for each amplification reaction, in various embodiments, the threshold selection process 500 proceeds to combine these values in such a way so as to permit a combination threshold to be associated with at least a portion of the data sets and amplification reactions in state 530. In one aspect, the combination threshold represents the threshold for a plurality of amplification reactions and may be obtained by averaging the thresholds for the individual reactions. Alternatively, a Gaussian analysis methodology can be used approximate the combination threshold in a manner that will be described in greater detail herein below. The Gaussian analysis methodology can further be used in weighting the distribution along each identified line segment to determine the confidence level or degree of certainty with which the combined threshold should fall along each point in the associated line segments.

Initially, in various embodiments, a Gaussian is calculated for each identified line segment corresponding to the predicted exponential regions for the plurality of amplification reactions under analysis. The formula illustrated by Equation #1 represents the Normal Gaussian distribution:

$$g(t) = \frac{1}{\sigma\sqrt{2\pi}} \exp\frac{(t-\mu)^2}{2\sigma^2} \qquad \text{Equation \#1}$$

In Equation #1, $\mu$ represents the mean of the distribution and $\sigma$ is its standard deviation. In one aspect, the results generated by this formula represent the certainty that the threshold lies at a particular fluorescence within the Gaussian distribution attributed to the vertical projection of the exponential region 125 in the log-linear plot. Furthermore, the standard deviation of the Gaussian is equated to the standard deviation of the y-coordinates of the data points in the exponential region 125 (also in the log-linear scale). It will be appreciated that the Gaussian can be determined in a number of ways such as by using an unaltered plot rather than a log-linear plot. Furthermore, the choice of standard deviation for the Gaussian can be readily changed and is not necessarily dependent upon the above-described log-linear selection method.

Upon determining a Gaussian for each amplification reaction, the process 500 proceeds to combine the Gaussians using a convolution method. Using a convolution equation, the two Gaussians may be combined to generate a new Gaussian whose mean is the average of the two original Gaussian means. As is known in the art, convolution of two Gaussians may be used in probability analysis to measure the effect of repeated independent trials for a single cumulative outcome. When applied to combining Gaussians from two amplification reactions, the data from each reaction is treated as a trial and the outcome is representative of the certainty of the location of the threshold. As shown below in Equation #2, a formula for calculating the convolution of two functions f and g may be applied to the Gaussians obtained for the amplification reactions.

$$(f * g)(t) = \int_{-\infty}^{\infty} f(x)g(t-x)dx \qquad \text{Equation \#2}$$

Following identification of the exponential ranges for each amplification reaction, the threshold is desirably selected 540 to be one which intersects the greatest number of exponential ranges for the collection of data sets to be analyzed together. The threshold is selected 540 by generating a Gaussian curve which measures the degree of certainty that the threshold value should be set at a particular fluorescence intensity. In one aspect, the threshold value is selected to be the fluorescence value representing the approximate center of the Gaussian curve. In this instance, the Gaussian curve is representative of a curve of certainty and the convolution of the data sets to be combined is itself a Gaussian distribution, the expected value of which is the average of all of the expected values for all convolved curves included in the data analysis.

Figure 6:
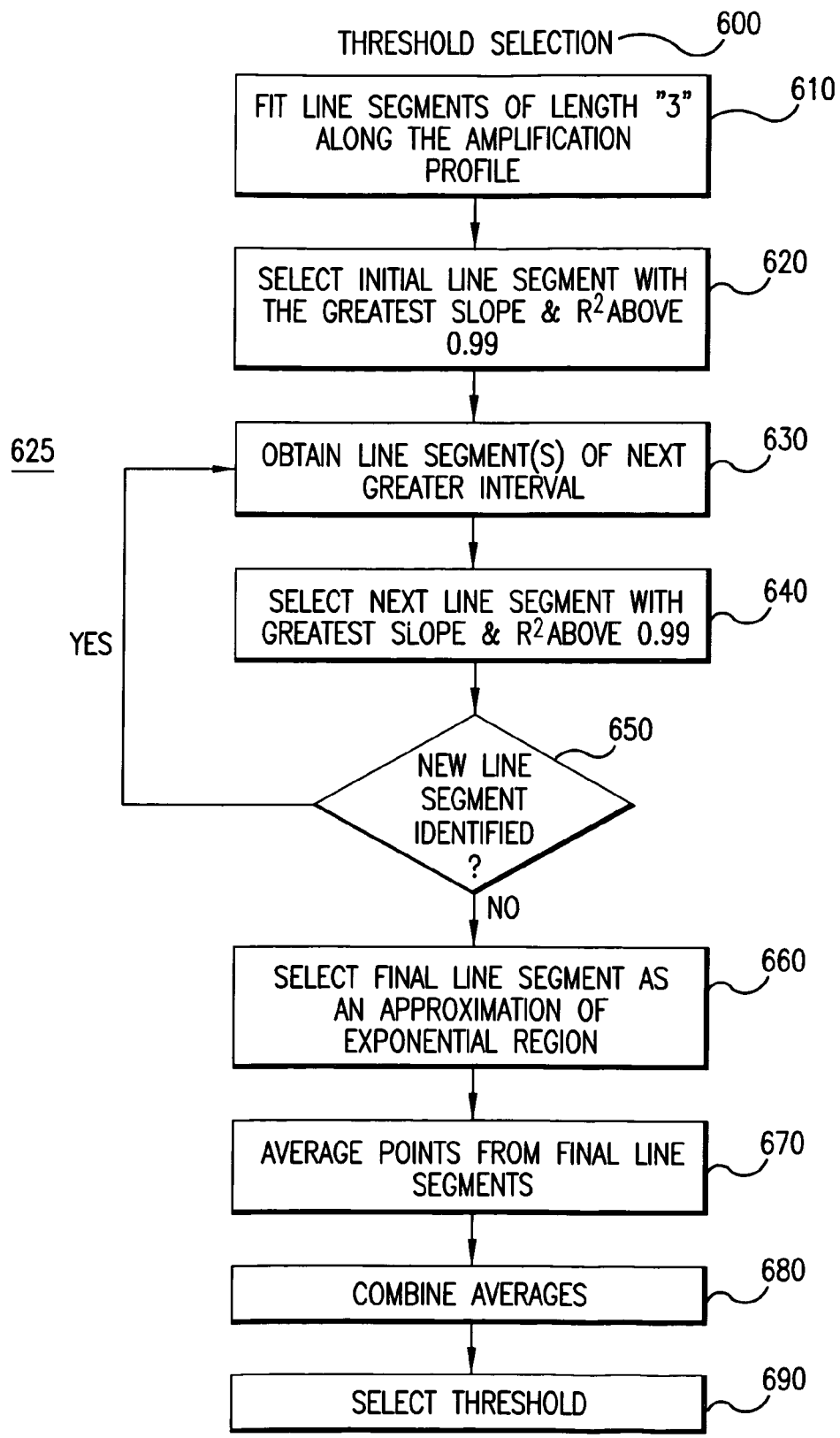
FIG. 6 is a flowchart of another embodiment of a threshold selection process.

FIG. 6 illustrates a process 600, according to various embodiments, for identification of the threshold value for a plurality of associated amplification reactions. In one aspect, the plurality of amplification reactions are performed in a parallel manner where amplification and subsequent fluorescence detection occurs in a multi-welled plate or dish. In such an experiment, the data from each of the individual reactions may be desirably evaluated with respect to one another for the purposes of determining values such as background fluorescence and threshold.

The process 600 begins by fitting line segments of a predetermined or selectable interval length along each amplification profile to be analyzed 610. Drawing, in part, from a known error analysis formula, statistically relevant parameters are identified which are useful in determining the quality of fit of the line segments. Equation #3 illustrates an exemplary probability analysis formula that relates a particular $r_0$ to the probability p that a series of N points are collinear. In this formula $\Gamma$ denotes the gamma function and $r^2$ is a measure of the goodness of fit. Based on this equation, an $r^2$ cutoff may be implemented in conjunction with the fluorescence data to determine a probability cutoff signifying the tolerance limits for line segment fitting. Additional details of the statistical analysis methods related to the probability analysis formula of Equation #3 can be found in *An Introduction to Error Analysis* by J. R. Taylor, University Science Books, 1982.

$$p = \frac{2\Gamma\left(\frac{N-1}{2}\right)}{\sqrt{\pi}\,\Gamma\left(\frac{N-2}{2}\right)} \int_{r_0}^{1} (1-r^2)^{\frac{N-4}{2}} dr \qquad \text{Equation \#3}$$

In general, in various embodiments, a predetermined interval length of "3" is initially used in the probability analysis, however, other values may be readily selected during the line fitting process. From the collection of line segments produced, the line segment with the greatest slope (m) and fit quality ($r^2$) is selected 620 to represent the exponential region 125 of the amplification profile 117. In one aspect, the process 600 selects the line segment having a fit quality that exceeds a designated probability cutoff value to aid in establishing a good fit between the line segment and the actual data points 130 of the amplification profile 117. For example, a fit quality cutoff of 0.99 indicates that the line segment has a statistical probability of at most a 1% chance that the selected line segment originated as a result of random noise. This manner of selection thus improves the quality of line segment selection and contributes to an increased level of confidence that the selection substantially represents the exponential region 125 of the amplification profile 117.

Following the initial line segment selection 620, the process 600 proceeds into a loop 625 to identify any other line segments which possess more desirable characteristics than the initial line segment. The loop begins by obtaining one or more line segments of a next interval length 630. The next interval length is typically incrementally selected, for example an interval length of "4" follows the initial interval length of "3". Using this newly selected interval length, a second line segment may be identified 640 which possesses the greatest slope of the newly identified line segments and still conforms to the selected fit quality cutoff. If a second line segment is identified which possesses a greater slope than the initial segment while maintaining acceptable fit quality, then the loop 625 is repeated with a new interval length greater than the previous selected length. The loop 625 continues until no new line segment can be identified 650 which conforms to the selected interval length and fit quality. At this point, the line segment having the greatest interval length is selected as the final line segment 660. The final line segment represents an approximation of the exponential region 125 for that particular amplification reaction.

For each final line segment, according to various embodiments, the fluorescence data points associated with the line are then identified and an average and standard deviation is calculated 670. In one aspect, the averaging and standard deviation calculations are based on a log-linear scale and Gaussian distributions are calculated according to the aforementioned equations. Subsequently, an average is determined over all amplification reactions to be included in the threshold determination 680. This combined average is obtained using the result of the individual averages for each of the amplification reactions where the Gaussians are convolved and the mean of the resulting Gaussian is determined as previously described. Finally, the results of this combined averaging is selected as the threshold value 690 for the selected group of amplification reactions. Alternatively, the combined average may be obtained by averaging the results for each of the individual reactions without performing a Gaussian analysis.

In order to aid in the assessment of the calculated threshold value and to increase the confidence that the value is appropriate, one or more metrics may be applied to the data. In certain embodiments, a first threshold evaluation metric comprises assessing the linearity of a standard curve, generated using known quantities of template. As will be appreciated by one of skill in the art, standard curve evaluation may be desirably used in experimental validation, unknown template quantitation and to assess the relative efficiency of the amplification reactions.

In one aspect, amplification standards are desirably included in one or more parallel amplification reactions and provide a means for determining if the calculated threshold conforms to an expected threshold for these reactions. Deviations in the calculated threshold from the expected threshold can be readily observed as a "bowing" or departure away from a theoretically linear standard curve. Additionally, the threshold value can be evaluated by determining the calculated values for known initial concentrations of template and comparing these values to the expected values. A good threshold value will show correspondence between the calculated template concentration and the known template concentration indicating that the threshold value is of high quality. Additional details of the formation and use of standard curves in assessment and validation of the amplification data will subsequently be described in greater detail herein below.

Figure 7A:
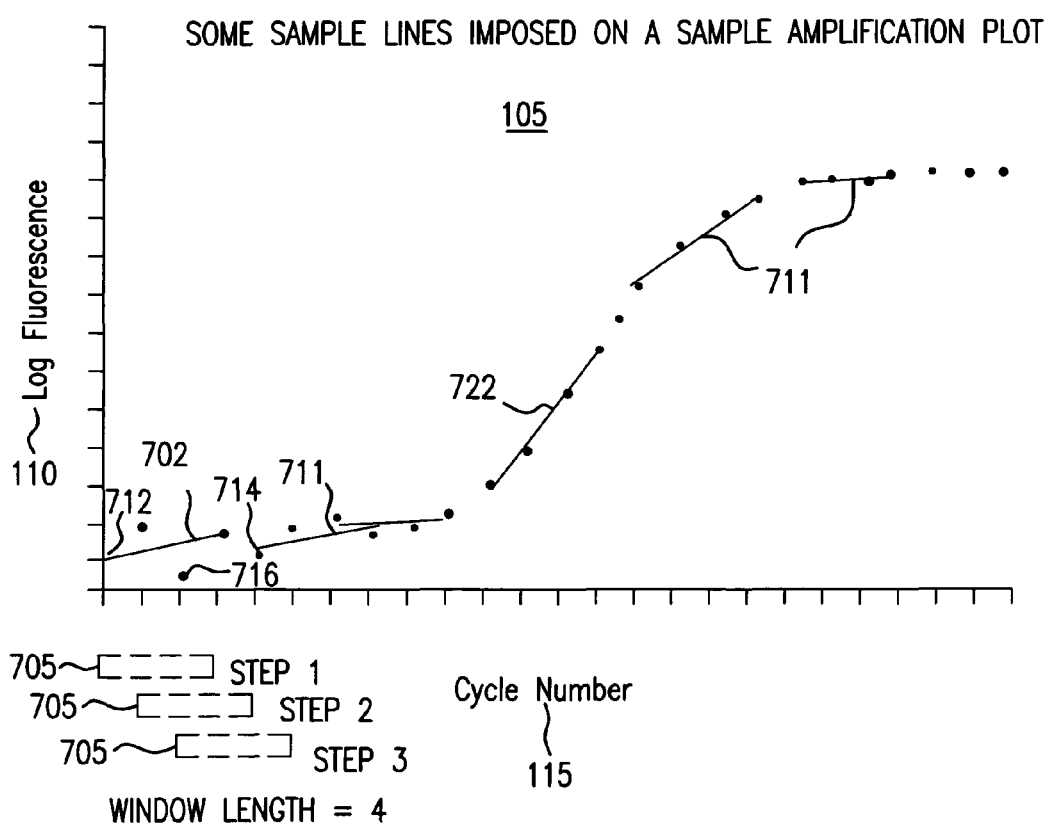
FIG. 7A is a graph illustrating a sliding window method for exponential region evaluation.

FIG. 7A provides a graphical illustration 700 of the threshold analysis methodology used to identify the line segment representative of the exponential region 125 of the amplification profile 117. As mentioned above, line segments 711 are fit to the graph of the fluorescence data 110 versus cycle number 115. Typically, this analysis takes place using the natural logarithm of the fluorescence data, however, the data in its original (non-log) form, or other suitable form, may also be utilized. The line fitting methods operate by fitting the plurality of line segments to the log-linear amplification plot 105 using a sliding window approach to analysis. The sliding window 705 begins with the first cycle for the amplification plot 105 and a first line 702 is fit to the selected data set. As line fitting analysis occurs in the sliding window the following values are identified and stored for each fitted line segment:

x: the x-value (cycle number) of the first point used to fit the line.
y: the y-value (fluorescence) of the first point used to fit the line.
b: the y-intercept of the fitted line.
m: the slope of the line.
L: the number of cycles spanned by the line.
$r^2$: the accuracy of fit.

The accuracy of fit ($r^2$) (see Equation 4) is further determined using the covariance of x and y denoted $V_{xy}$ (see Equation 5) which is divided by the variance $V_{xx}$ of x (see Equation 6) and by the variance $V_{yy}$ of y (see Equation 7). The results of this calculation are then stored for subsequent evaluation.

Equation 4:
$$r^2 = \frac{V_{xy}^2}{V_{xx} * V_{yy}}$$

Equation 5:
$$\mathrm{Cov}_{xy} = \frac{\sum xy - \frac{\sum x \sum y}{n}}{n-1}$$

Equation 6:
$$V_{xx} = \frac{\sum x^2 - \frac{1}{n}(\sum x)^2}{n}$$

Equation 7:
$$V_{yy} = \frac{\sum y^2 - \frac{1}{n}(\sum y)^2}{n}$$

Upon completion of the first line segment 702 analysis the sliding window 705 moves forward one data point. The forward movement of the sliding window causes a first data point 712 to drop out of the window 705 and a new data point 714 to enter into the window 705. A new line segment is then fit to the data in the window 705 using a similar set of calculations as described above (line segment not shown in the figure). The window 705 is subsequently incremented again to the next data point 716 and the process is repeated until the window 705 has progressed through the entire set of fluorescence data points. In this manner, a complete collection of line segments can be obtained for a designated window size (length=4 in the illustration). The aforementioned slope analysis steps discussed in connection with FIG. 6 can then be used to identify the best line segment 722 having the greatest slope with an acceptable accuracy of fit. Subsequently, the entire window sliding process is repeated for a next incremental window size to identify a second plurality of line segments from which the best line segment is selected (if present). In this manner the best overall line segment can be identified which is selected as the approximation of the exponential region 125 of the amplification profile 117 under analysis.

The aforementioned methods for determining the threshold value based on amplification reaction data are applicable to a number of PCR-based quantitation strategies including: quantitative PCR, real-time PCR, quantitative competitive PCR, and other related technologies which utilize amplification reaction data to determine the concentration of template initially present in the reaction. In general, in each of the aforementioned technologies, amplification reactions may be characterized by the point in time during cycling when amplification of a PCR product is detectable rather than the amount of PCR product accumulated after a fixed number of cycles.

Following baseline and threshold analysis, a threshold cycle ($C_T$) may be identified. The threshold cycle is defined as the cycle number (which may be fractional) at which the observed fluorescence intersects the calculated threshold. Quantitation of the amount of target in one or more associated amplification reactions may then be accomplished by measuring the threshold cycle and using a standard curve to determine the starting copy number or initial concentration of the template.

In one aspect, a standard curve may be generated by applying the threshold identification methodology to calculate a threshold cycle ($C_T$) for each of a plurality of amplification reactions having a substantially known template concentration. As previously described, the threshold cycle ($C_T$) for each template may be further identified by determining the fractional cycle number at which the intensity signal crosses the identified threshold determined by the threshold identification methodology.

Figure 7B:
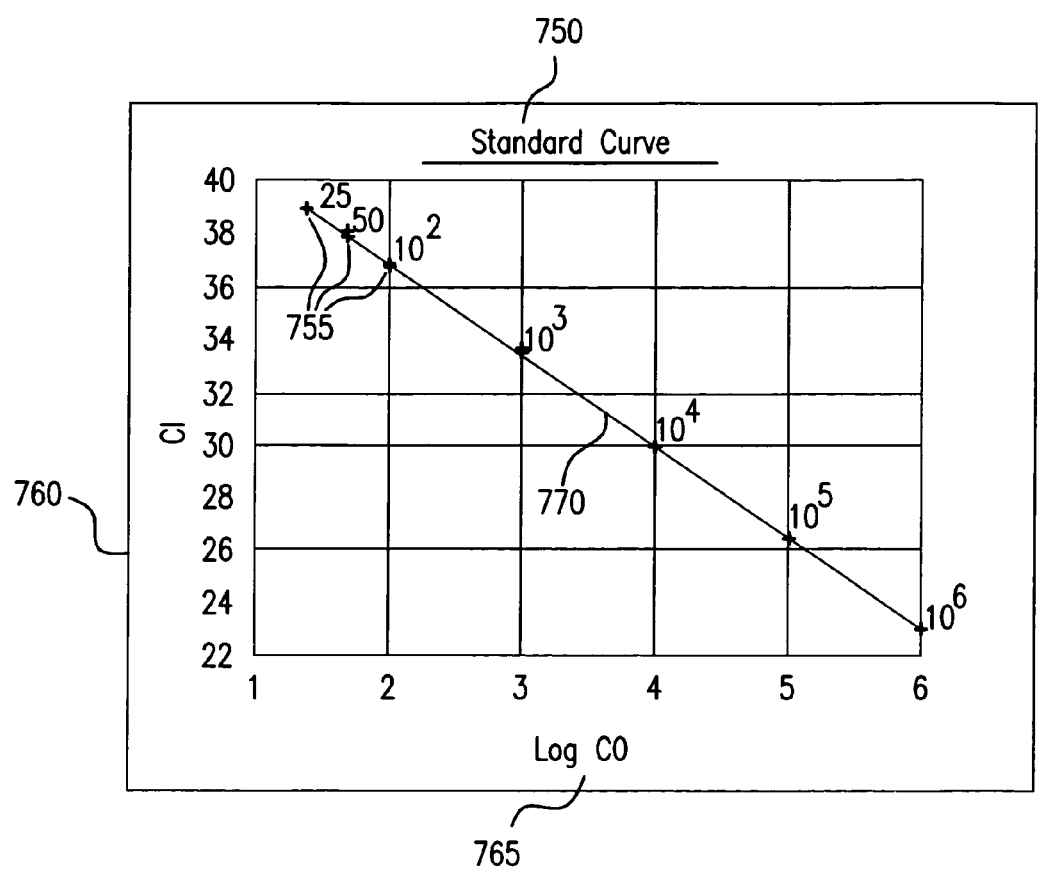
FIG. 7B is a graph illustrating an exemplary standard curve obtained for a plurality of amplification reactions.

FIG. 7B illustrates an exemplary standard curve 750 generated from amplification reaction data for templates of known initial concentration. Each standard data point 755 is obtained by associating the calculated threshold cycle ($C_T$) (plotted along the y-axis 760) with the initial template concentration (expressed as a function of the log of the template copy number and plotted along the x-axis 765). Standard data points 755 are shown for duplicate amplification reactions obtained for template concentrations having concentrations of approximately $10^6$, $10^5$, $10^4$, $10^3$, $10^6$, 50, and 25 copies respectively.

Linear regression using the standard data points 755 yields an approximation line 770 that indicates a substantial degree of linearity in the standard curve 750. Such linearity of the standard curve 750 further implies that the selected threshold for these associated amplification reactions has been appropriately selected within the approximated exponential region for each amplification reaction.

Furthermore, using the exemplary data contained in the standard curve, a linear regression test ($r^2$) may be used to determine the relative linearity within the data (found to be greater than 0.99 in the case of the exemplary data). In general, regression values approaching 1.0 are desirable as they indicate substantial linearity which serves to validate that the appropriate threshold and threshold cycle have been selected.

As will be appreciated by one of skill in the art, upon determination of the appropriate threshold cycle(s) this information may be subsequently used to determine the initial concentration of template. In one aspect, amplification progression in the exponential region may be described by the equation:

$$Q_n = Q_o(R)^c \qquad \text{Equation 8:}$$

In this equation $Q_n$ represents the amount of target sequence at cycle c, $Q_o$ is the initial amount of template, and R is the relative efficiency of amplification. By integrating this equation with the threshold cycle a linear relationship can be identified and shown by the equation:

$$C_T = [\log(T) - \log(Q_0)]/\log(R) \qquad \text{Equation 9:}$$

This equation reflects the characteristics of the standard curve and can subsequently be used to calculate that the amount of template initially present in the amplification reaction. Additional details regarding quantitation methods based on the threshold cycle number can be found in *Real Time Quantitative PCR*, Genome Research, Cold Spring Harbor Laboratory Press, 1996.

In one aspect, the aforementioned methodologies may be applied to an automated quantitation process wherein an application or computer program is configured to receive the results of the baseline and threshold determinations to analyze each amplification reaction. Such an automated method is particularly well suited for high-throughput quantitation of RNA or DNA templates and provides improved sensitivity and accuracy over conventional methods.

Figure 8:
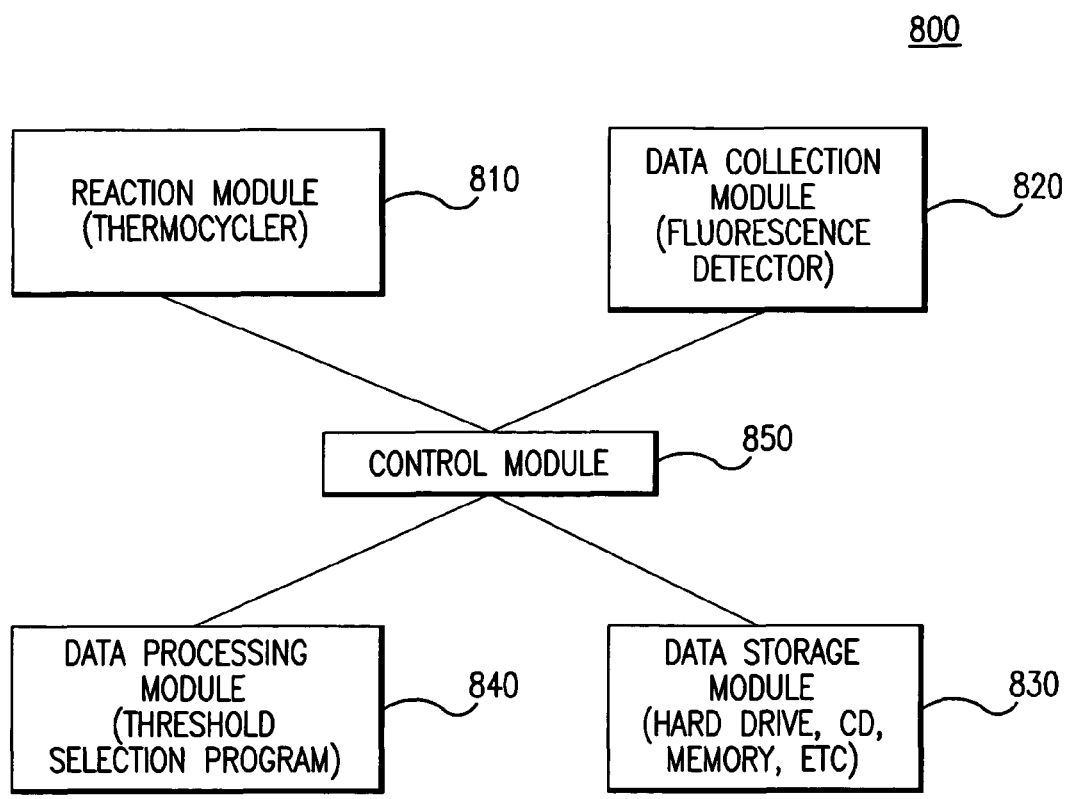
FIG. 8 is a block diagram of a quantitative PCR system incorporating an automated threshold detection module.

FIG. 8 illustrates a system 800, according to various embodiments, for performing quantitative PCR in conjunction with the aforementioned baseline and threshold analysis methodologies. In one aspect, the system 800 comprises a plurality of modules interconnected or networked by way of a communications medium to substantially automate the analysis. A reaction module 810 receives the samples to undergo amplification and provides the necessary hardware to regulate the temperature of the samples in a desired manner. For example, reaction module 810 may comprise a thermocycler or other hardware device capable of being programmed with a particular method which defines controlled heating and cooling steps executed over designated time intervals.

The system 800 further comprises, in various embodiments, a data collection module 820 that detects and measures the fluorescence generated for each amplification reaction. The data collection module 820 may be configured to read the fluorescence directly while the reaction module 810 is in operation or alternatively samples from the amplification reactions may be withdrawn and measured separately by the data collection module 820. In one aspect, the data collection module 820 comprises a fluorescence detector configured to measure fluorescence at the emission wavelength for a particular label or reporter incorporated into the amplification reaction.

The data collection module 820, according to various embodiments, can transmit the fluorescence data to a data storage module 830 responsible for archiving the fluorescence results for each reaction over the specified time course. The data storage module 830 may store the data in numerous different forms and configurations including tables, charts, arrays, spreadsheets, databases, and the like. In one aspect, the data storage module 830 receives the results from many different experiments and presents the data to other modules responsible for the subsequent comparison and analysis of the data. Furthermore, the data storage module 830 stores the results of the quantitation analysis which may be output as needed or requested.

A data processing module 840, according to various embodiments, receives selected data from the data storage module 830 or alternatively from the data collection module 820 and performs the operations associated with noise determination and threshold selection. These analytical methods may be implemented using a computer program which comprises a plurality of functions designed to manipulate the data and generate requested information including: baseline noise level determination, exponential region identification, threshold selection and combination, quantitative analysis, and other related analytical methods. In one aspect, the data processing module 840 is designed to operate in a user-independent manner where all of the calculations and analytical tasks are performed without the need for the user to manually assess or interpret the data.

Finally, in certain embodiments, a control module 850 may be incorporated into the system 800 to provide a means for integrating the tasks associated with each module. The control module 850 may be configured to communicate with each module of the system 800 and coordinates system-wide activities to facilitate the automated quantitative PCR analysis. Additionally, the control module 830 may monitor each module to verify their proper function and provide a user interface for interacting with the various components of the system 800.

The computer program listing appendix illustrates the C++ source code for an exemplary program that may be used to implement the data analysis methods used for baseline determination, exponential region identification, and threshold selection. In one aspect the program is configured to receive data from a text file or other data file type which contains amplification data for one or more amplification reactions. After performing the analysis, the program outputs the results of the threshold for each amplification reaction, as well as, a combined threshold value. Briefly described the program first identifies the end of the noise region for each amplification reaction, using the aforementioned monotonicity test. The program then fits a plurality of lines to regions of this data, each line having a length from three to seven cycles by default. As previously described this portion of the program is used to identify part of the exponential region 125 by finding a line segment with a high slope and high accuracy of fit. The program then extends this line, maximizing the slope, as long as the accuracy threshold can be maintained.

Upon identification of the exponential region 125 for each amplification reaction, the program assigns a Gaussian probability distribution to the exponential region 125. The thresholds for each amplification reaction are then combined to generate a single composite threshold using the Gaussian convolution method. The identified thresholds are then returned to the user. As previously described above, threshold identification may also be performed by averaging the threshold for each of the individual amplification reactions to obtain the combined threshold.

Within the program, a plurality of user-configurable parameters are defined which alter the functionality of the program and the manner in which the threshold analysis is conducted. These parameters include:

Filename: The name of the text file which contains the fluorescence data to be used in the analysis.

NUMWELLS: The number of amplification reactions to be included in the analysis.

RUNLENGTH: The maximum number of cycles for which the amplification reaction is allowed to run.

FIRST, LAST: The minimum and maximum number of cycles spanned by the line segments on the first pass of the sliding window. Increasing this value may improve the accuracy of the identified threshold.

MINR: This is the limit of acceptability for accuracy of fit ($r^2$). The closer this value is to 1, the better the fit required to extend the line segment defining the exponential region. Increasing this value causes the program to require an exponential region to be more linear.

In addition to these values the following values are also defined and are used as previously described in conjunction with the sliding window line segment analysis.

x: the x-value (cycle number) of the first point used to fit the line.

y: the y-value (fluorescence) of the first point used to fit the line.

b: the y-intercept of the fitted line.

m: the slope of the line.

L: the number of cycles spanned by the line.

$r^2$: the accuracy of fit.

The principal functions of the program include: (a) parsing the input text file to determine the fluorescence data to be used in the analysis; (b) analyzing the fluorescence data for each amplification plot; (c) choosing the best line (threshold) for each amplification plot; (d) combining the thresholds into a single combined threshold; and (e) outputting the results of the analysis. In performing the abovementioned functions, the program takes into account the manner in which the data is formatted and presented. For example, when performing the line fitting calculations used to identify the exponential region and threshold, the data may presented in a raw form which is subsequently converted to a log-linear version similar to that described in relation to FIGS. 7A and 7B. Conversion of the data is this manner may be performed automatically or the program may be modified to accept or utilize amplification data presented in other formats (i.e. linear-linear version of the data). As will be appreciated by one of skill in the art this program may be further modified to include additional functionality and may be integrated into other analytical methods used to determine the initial concentration of sample template used in the amplification reaction.

Although the above-disclosed embodiments of the present invention have shown, described, and pointed out the fundamental novel features of the invention as applied to the above-disclosed embodiments, it should be understood that various omissions, substitutions, and changes in the form of the detail of the devices, systems, and/or methods illustrated may be made by those skilled in the art without departing from the scope of the present invention. Consequently, the scope of the invention should not be limited to the foregoing description, but should be defined by the appended claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

What is claimed is:

1. A method for determining a threshold for a PCR amplification reaction, comprising:

performing a quantitative PCR amplification reaction in a thermocycler system for at least one target sample template;

acquiring detection information generated for the quantitative PCR amplification of the at least one target sample template;

analyzing at least a subset of a plurality of intervals of the detection information to identify an exponential region; said intervals having a different length, the analyzing comprising:
- (a) performing a regression fit on a plurality of successive intervals of the at least one subset using a first interval length;
- (b) identifying a first best-fit line by evaluating the slopes of the plurality of successive intervals of the subset having the first interval length;
- (c) identifying the exponential region by repeating steps (a) through (b) on the plurality of successive intervals of the at least one subset, wherein the interval length is successively incremented until an overall best-fit line having the greatest slope is determined; and determining a threshold for the quantitative PCR amplification of the at least one target sample template, wherein the determination of the threshold is based on the identified exponential region.

2. The method of claim 1, wherein the intervals comprise intervals over cycles of the at least one amplification reaction.

3. The method of claim 2, wherein the intervals comprise between approximately 3 and 10 cycles.

4. The method of claim 1, wherein a threshold cycle is identified where the detection information intersects the determined threshold.

5. The method of claim 4, wherein the threshold cycle is used to determine the initial target sequence concentration.

6. A method for quantitative polymerase chain reaction-based analysis wherein a plurality of sample templates are amplified using a fluorescent reporter construct configured to monitor the progress of amplification, the method comprising:

acquiring fluorescence data generated by the fluorescent reporter construct resulting from the amplification of each sample template;

generating amplification profiles from the fluorescence data acquired for each sample template;

determining an exponential threshold for each of the amplification profiles, the exponential threshold being associated with an exponential region of the corresponding amplification profile; and generating a combined exponential threshold, the combined exponential threshold being associated with a region within each of the amplification profiles corresponding to exponential amplification of the corresponding sample template.

7. The method of claim 6, wherein determining an exponential threshold for each of the amplification profiles comprises applying a Gaussian approximation to each of the amplification profiles to identify an exponential region of amplification corresponding to the exponential threshold for each amplification profile.

8. The method of claim 7, wherein the Gaussian approximation further comprises:

identifying a plurality of line segments, each of the plurality of line segments having an associated slope and a fit metric indicating a degree of fit of the line segment to fluorescence data; and comparing the slope and fit metric for each of the line segments to identify a line segment corresponding to the exponential threshold having the greatest slope and minimum fit metric.

9. The method of claim 8, wherein the minimum fit metric is selected to increase the probability that the line segment reflects the exponential region of the associated amplification profile.

10. The method of claim 9, wherein the minimum fit metric comprises a probability of at least 99%.

11. The method of claim 6, wherein the generating a combined exponential threshold comprises performing a Gaussian convolution of the exponential thresholds obtained for each of the sample templates.

12. The method of claim 11, wherein performing a Gaussian convolution comprises averaging the exponential thresholds obtained for each of the sample templates.

13. The method of claim 12, wherein the mean of the Gaussian convolution is representative of the combined exponential threshold.

14. A system for identifying an exponential threshold to be used in the analysis of an amplification reaction, comprising:

a data collection module that collects detection information generated by the detection of at least one amplification reaction using a target sequence having an initial concentration and containing a detectable reporter construct, the detection information indicating a change in the concentration of the target sequence during the amplification reaction; and a data processing module, the data processing module configured to analyze at least a subset of the detection information to identify an exponential threshold associated with an exponential region of the subset where the target sequence concentration increases in a exponential manner, the analyzing comprising analyzing a plurality of intervals of the subset having a different length.

15. The system of claim 14, wherein the analyzing the plurality of intervals further comprises:
- (a) performing a regression fit on a first plurality of successive intervals of the subset having a first interval length;
- (b) identifying a first best-fit line by evaluating the slopes of the first plurality of successive intervals of the subset;
- (c) identifying a first best-fit line by identifying a greatest slope generated in step (b) that also satisfies a selected fit quality;
- (d) selecting a second plurality of successive intervals of the subset having a second interval length;
- (e) performing a second regression fit on the second plurality of successive intervals of the subset according to steps (a) through (c) to generate a second best-fit line;
- (f) identifying an overall best-fit line by selecting the one of the first best-fit line and the second best-fit line having the greater slope; and
- (g) defining the exponential region by repeating steps (a) through (f) to identify an overall best-fit line having the greatest slope.

16. The system of claim 15, wherein the intervals comprise intervals over cycles of the at least one amplification reaction.

17. The system of claim 16, wherein the intervals comprise between approximately 3 and 10 cycles.

18. The system of claim 14, wherein the data processing module is further configured to identify a threshold cycle where the detection information exceeds the exponential threshold.

19. The system of claim 18, wherein the threshold cycle is used to determine the initial target sequence concentration.

20. The system of claim 14, wherein the detectable reporter construct comprises a fluorescence label and the detection information comprises a plurality of detected fluorescence intensity values.

21. The system of claim 14, wherein the at least one amplification reaction comprises a plurality of amplification cycles.

22. The system of claim 14, wherein the at least one amplification reaction comprises a polymerase chain reaction.

23. The system of claim 22, wherein the amplification reaction analysis is applied to analyzing quantitative polymerase chain reaction data.

24. The system of claim 22, wherein the amplification reaction analysis is applied to analyzing quantitative competitive polymerase chain reaction data.

25. A system for quantitative polymerase chain reaction-based analysis wherein a plurality of sample templates are amplified using a fluorescent reporter construct configured to monitor the progress of amplification, comprising:
- a data collection module that collects amplification profiles generated from fluorescence data generated by the fluorescent reporter construct resulting from the amplification of each sample template; and
- a data processing module, the data processing module being configured to
- determine an exponential threshold for each of the amplification profiles, the exponential threshold being associated with an exponential region of the corresponding amplification profile, and
- generate a combined exponential threshold, the combined exponential threshold being associated with a region within each of the amplification profiles corresponding to exponential amplification of the corresponding sample template.

26. The system of claim 25, wherein the data processing module is further configured to determine an exponential threshold for each of the amplification profiles by applying a Gaussian approximation to each of the amplification profiles to identify an exponential region of amplification corresponding to the exponential threshold for each amplification profile.

27. The system of claim 26, wherein the data processing module is further configured to apply a Gaussian approximation by:
- identifying a plurality of line segments, each of the plurality of line segments having an associated slope and a fit metric indicating a degree of fit of the line segment to fluorescence data; and
- comparing the slope and fit metric for each of the line segments to identify a line segment corresponding to the exponential threshold having the greatest slope and minimum fit metric.

28. The system of claim 27, wherein the minimum fit metric is selected to increase the probability that the line segment reflects the exponential region of the associated amplification profile.

29. The system of claim 28, wherein the minimum fit metric comprises a probability of at least 99%.

30. The system of claim 25, wherein the data processing module is further configured to generate the combined exponential threshold by performing a Gaussian convolution of the exponential thresholds obtained for each of the sample templates.

31. The system of claim 30, wherein performing a exponential threshold analysis comprises averaging the exponential thresholds obtained for each of the sample templates.

32. The system of claim 31, wherein the mean of the Gaussian convolution is representative of the combined exponential threshold.

33. A system for analyzing data associated with the amplification of sample templates, the system comprising:
- a reaction module where amplification of the sample templates takes place using a detectable reporter label;
- a data collection module that detects reporter label intensities over the course of the amplification and reports the detected intensities; and
- a data processing module that receives the detected intensities, associates the detected intensities with a data set, and performs an exponential region analysis on the data set to generate a combined exponential threshold for each of the sample templates associated with a region where each sample template amplification is increasing in a exponential manner.

34. The system of claim 33, wherein the data processing module generates the combined exponential threshold by performing a Gaussian convolution of the exponential thresholds for each of the sample templates.

35. A method for quantitative polymerase chain reaction (PCR)-based analysis wherein a plurality of sample templates are amplified using a fluorescent reporter construct to monitor the progress of amplification, the method comprising:
- performing a plurality of Quantitative PCR amplification reactions in a thermocycler system for a plurality of sample templates;
- acquiring fluorescence data corresponding to the amplification for each of the plurality of sample templates;
- analyzing the fluorescence data to generate a plurality of amplification profiles;
- applying a threshold approximation to each of the amplification profiles to identify an exponential region of amplification and a corresponding exponential threshold for each sample template corresponding to a period during the amplification where the sample template undergoes exponential amplification; and
- averaging the exponential thresholds to generate a combined exponential threshold.

36. The method of claim 35, wherein the threshold approximation comprises:
- identifying a plurality of line segments each having an associated slope and fit quality that corresponds to a degree of fit of the line segment to the fluorescence data of the amplification profile; and
- comparing the slope and fit quality for each of the line segments to identify an exponential threshold corresponding to the line segment which possesses the greatest slope and maintains a desired fit quality.

37. The method of claim 36, wherein the desired fit quality is selected to increase the probability that the line segment resides within the exponential region of the amplification profile.

38. The method of claim 36, wherein the desired fit quality is 99%.

* * * * *